United States Patent
Baril et al.

(10) Patent No.: US 10,993,721 B2
(45) Date of Patent: May 4, 2021

(54) SURGICAL CLIP APPLIER

(71) Applicant: Covidien LP, Mansfield, MA (US)

(72) Inventors: Jacob C. Baril, Norwalk, CT (US); Roy J. Pilletere, North Haven, CT (US); Justin Thomas, New Haven, CT (US); Matthew A. Dinino, Newington, CT (US)

(73) Assignee: COVIDIEN LP, Mansfield, MA (US)

( * ) Notice: Subject to any disclaimer, the term of this patent is extended or adjusted under 35 U.S.C. 154(b) by 233 days.

(21) Appl. No.: 16/262,073

(22) Filed: Jan. 30, 2019

(65) Prior Publication Data

US 2019/0328389 A1   Oct. 31, 2019

Related U.S. Application Data

(60) Provisional application No. 62/662,284, filed on Apr. 25, 2018.

(51) Int. Cl.
*A61B 17/10* (2006.01)
*A61B 17/00* (2006.01)
*A61B 17/08* (2006.01)

(52) U.S. Cl.
CPC ........ *A61B 17/10* (2013.01); *A61B 17/00234* (2013.01); *A61B 17/083* (2013.01);
(Continued)

(58) Field of Classification Search
CPC . A61B 17/10; A61B 17/00234; A61B 17/083; A61B 2017/00367;
(Continued)

(56) References Cited

U.S. PATENT DOCUMENTS 3,120,230 A   2/1964   Skold
3,363,628 A   1/1968   Wood
(Continued)

FOREIGN PATENT DOCUMENTS

AU    2013254887 A1   11/2013
CA      1163889 A      3/1984
(Continued)

OTHER PUBLICATIONS

European Office Action corresponding to EP 12 152 989.5 dated May 4, 2015.
(Continued)

*Primary Examiner* — George J Ulsh
*Assistant Examiner* — Andrew P. Restaino

(57) ABSTRACT

A surgical clip applier includes a handle assembly and an elongated assembly configured to releasably engage the handle assembly. The handle assembly includes a trigger and a drive bar wherein pivoting of the trigger through a full actuation stroke translates the drive bar through a full drive distance. The drive bar has a magnetic distal end portion. The elongated assembly includes an inner drive assembly including a magnetic proximal end portion. Upon engagement of the elongated assembly with the handle assembly, the magnetic proximal end portion of the inner drive assembly is configured to attract the magnetic distal end portion of the drive bar to move the drive bar and pivot the trigger such that the trigger is pivotable through a reduced actuation stroke to translate the drive bar through a reduced drive distance.

12 Claims, 4 Drawing Sheets

(52) U.S. Cl.
CPC ............... *A61B 2017/0042* (2013.01); *A61B 2017/00367* (2013.01)

(58) Field of Classification Search
CPC .... A61B 2017/0042; A61B 2017/0046; A61B 2017/00477; A61B 2017/00876; A61B 17/1285; A61B 17/29; A61B 2017/2902
See application file for complete search history.

(56) References Cited

U.S. PATENT DOCUMENTS

| | | |
|---|---|---|
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,226,242 A | 10/1980 | Jarvik |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |

(56) References Cited

U.S. PATENT DOCUMENTS

| | | |
|---|---|---|
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |

(56) References Cited

U.S. PATENT DOCUMENTS

| | | |
|---|---|---|
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns |
| 7,488,335 B2 | 2/2009 | Sgro |
| 7,510,562 B2 | 3/2009 | Lindsay |
| 7,552,853 B2 | 6/2009 | Mas et al. |

(56) References Cited

U.S. PATENT DOCUMENTS

| | | |
|---|---|---|
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,048,088 B2 | 11/2011 | Green et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |

(56) References Cited

U.S. PATENT DOCUMENTS

| | | |
|---|---|---|
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,828,023 B2 | 9/2014 | Neff et al. |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,972 B1 | 3/2016 | Patel et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,810 B2 | 9/2016 | Cappola |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,526,565 B2 | 12/2016 | Strobl |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2002/0123742 A1 | 9/2002 | Baxter et al. |
| 2003/0014060 A1 | 1/2003 | Wilson et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0097970 A1 | 5/2004 | Hughett |
| 2004/0097971 A1 | 5/2004 | Hughett |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |

(56) References Cited

U.S. PATENT DOCUMENTS

| | | |
|---|---|---|
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0079115 A1 | 4/2006 | Aranyi |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0124485 A1 | 6/2006 | Kennedy |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0204115 A1 | 8/2009 | Dees, Jr. et al. |
| 2009/0209946 A1 | 8/2009 | Swayze |
| 2009/0228023 A1 | 9/2009 | Cui |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2009/0326558 A1 | 12/2009 | Cui et al. |
| 2010/0089970 A1 | 4/2010 | Smith et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0054498 A1 | 3/2011 | Monassevitch et al. |
| 2011/0087220 A1 | 4/2011 | Felder et al. |
| 2011/0087268 A1 | 4/2011 | Livneh |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0116366 A1* | 5/2012 | Houser ............... A61B 34/25 606/1 |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0041379 A1 | 2/2013 | Bodor et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175303 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2013/0325057 A1 | 12/2013 | Larson et al. |
| 2014/0005678 A1 | 1/2014 | Shelton, IV et al. |
| 2014/0074143 A1 | 3/2014 | Fitzgerald et al. |
| 2014/0188159 A1 | 7/2014 | Steege |
| 2014/0263565 A1 | 9/2014 | Lytle, IV et al. |
| 2014/0276970 A1 | 9/2014 | Messerly et al. |
| 2014/0371728 A1 | 12/2014 | Vaughn |
| 2015/0032131 A1 | 1/2015 | Sorrentino et al. |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2016/0004956 A1 | 1/2016 | Reynolds et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |

(56) References Cited

U.S. PATENT DOCUMENTS

| | | |
|---|---|---|
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | |
|---|---|---|
| CN | 103251441 A | 8/2013 |
| CN | 104605911 B | 2/2017 |
| DE | 20 2005 001664 U1 | 5/2005 |
| DE | 202007003398 U1 | 6/2007 |
| DE | 202009006113 U1 | 7/2009 |
| EP | 0000756 A1 | 2/1979 |
| EP | 0406724 A1 | 1/1991 |
| EP | 0514139 A2 | 11/1992 |
| EP | 0732078 A2 | 9/1996 |
| EP | 1769757 A1 | 4/2007 |
| EP | 2599447 A2 | 6/2013 |
| EP | 3132756 A1 | 2/2017 |
| EP | 3178408 A1 | 6/2017 |
| EP | 3476331 A1 | 5/2019 |
| GB | 2073022 A | 10/1981 |
| JP | 2003033361 A | 2/2003 |
| JP | 2006154230 A | 6/2006 |
| JP | 2006277221 A | 10/2006 |
| JP | 2008017876 A | 1/2008 |
| JP | 2011186812 A | 9/2011 |
| JP | 2013166982 A | 8/2013 |
| WO | 9003763 A1 | 4/1990 |
| WO | 0042922 A1 | 7/2000 |
| WO | 0166001 A2 | 9/2001 |
| WO | 0167965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017084000 A1 | 5/2017 |
| WO | 2017146138 A1 | 8/2017 |

OTHER PUBLICATIONS

Australian Office Action corresponding to AU 2009212759 dated May 7, 2015.
Chinese Office Action corresponding to Int'l Appln No. CN 201210212642.9 dated Jun. 3, 2015.
European Office Action corresponding to Int'l Appln No. EP 04 719 757.9 dated Jun. 12, 2015.
European Office Action corresponding to Int'l Appln No. EP 13 166 382.5 dated Jun. 19, 2015.
Japanese Office Action corresponding to Int'l Application No. JP 2010-226908 dated Jun. 26, 2015.
Extended European Search Report corresponding to Int'l Application No. EP 15 15 5024.1 dated Jul. 17, 2015.
Extended European Search Report corresponding to Int'l Application No. EP 14 19 2026.4 dated Jul. 17, 2015.
Japanese Office Action corresponding to Int'l Application No. JP 2011-160126 dated Aug. 10, 2015.
Extended European Search Report corresponding to Int'l Application No. EP 14 15 0321.9 dated Sep. 23, 2015.
Extended European Search Report corresponding to Int'l Application No. EP 11 25 0675.3 dated Oct. 7, 2015.
Extended European Search Report corresponding to Int'l Application No. EP 11 25 0674.6 dated Oct. 7, 2015.
Extended European Search Report corresponding to Int'l Application No. EP 12 19 3447.5 dated Oct. 19, 2015.
Canadian Office Action corresponding to Int'l Application No. CA 2,675,875 dated Oct. 26, 2015.
Japanese Office Action corresponding to Int'l Application No. JP 2015-005629 dated Oct. 28, 2015.
Japanese Office Action corresponding to Int'l Application No. JP 2014-245081 dated Oct. 28, 2015.
Canadian Office Action corresponding to Int'l Application No. CA 2,675,921 dated Oct. 30, 2015.
Chinese Office Action corresponding to Int'l Application No. CN 201210555570.8 dated Nov. 2, 2015.
Canadian Office Action corresponding to Int'l Application No. CA 2,676,309 dated Nov. 3, 2015.
Canadian Office Action corresponding to Int'l Application No. CA 2,676,211 dated Nov. 24, 2015.
Canadian Office Action corresponding to Int'l Application No. CA 2,676,547 dated Nov. 25, 2015.
Extended European Search Report corresponding to Int'l Application No. EP 15 17 3809.3 dated Nov. 25, 2015.
Chinese Office Action corresponding to Int'l Application No. CN 201210586814.9 dated Dec. 2, 2015.
Extended European Search Report corresponding to Int'l Application No. EP 12 17 2940.4 dated Dec. 14, 2015.
Chinese First Office Action corresponding to Int'l Appln. No. CN 201210586826.1 dated Dec. 30, 2015.
Extended European Search Report corresponding to Int'l Appln. No. EP 15 18 5362.9 dated Feb. 12, 2016.
Extended European Search Report corresponding to Int'l Appln. No. EP 12 19 7813.4 dated Mar. 7, 2016.
Canadian Office Action corresponding to Int'l Appln. No. CA 2,676,465 dated Mar. 8, 2016.
Japanese Office Action corresponding to Int'l Appln. No. JP 2014-245081 dated Mar. 18, 2016.
Japanese Office Action corresponding to Int'l Appln. No. JP 2015-005629 dated Mar. 18, 2016.
Extended European Search Report corresponding to Int'l Appln. No. EP 15 19 3549.1 dated Mar. 22, 2016.
International Search Report and Written Opinion corresponding to Int'l Appln. No. PCT/CN2015/082199 dated Mar. 31, 2016.
Extended European Search Report corresponding to Int'l Appln. No. EP 15 19 7251.0 dated Apr. 8, 2016.
Extended European Search Report corresponding to Int'l Appln. No. EP 16 15 0739.7 dated May 17, 2016.
Canadian Office Action corresponding to Int'l Appln. No. CA 2,716,672 dated May 31, 2016.
Canadian Office Action corresponding to Int'l Appln. No. CA 2,717,448 dated May 31, 2016.

(56) References Cited

OTHER PUBLICATIONS

Canadian Office Action corresponding to Int'l Appln. No. CA 2,721,951 dated Jun. 1, 2016.
Partial European Search Report corresponding to Int'l Appln. No. EP 16 15 0287.7 dated Jun. 16, 2016.
Chinese Second Office Action corresponding to Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
European Office Action corresponding to European Appln. No. EP 16 15 9324.9 dated Aug. 7, 2017.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
International Search Report corresponding to Int'l Patent Appln. PCT/US2018/050316 dated Dec. 31, 2018.
International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.
The extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).
The International Search Report corresponding to International Application No. PCT-US08-59859, completed Sep. 14, 2008; dated Sep. 18, 2008; (2 Pages).
The extended European Search Report corresponding to European Application No. EP 07 25 3807.7, completed Nov. 7, 2008; dated Nov. 26, 2008; (11 Pages).
The extended European Search Report corresponding to European Application No. EP 09 25 2049.3, completed Dec. 11, 2009; dated Jan. 12, 2010; (3 Pages).
The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).
The extended European Search Report corresponding to European Application No. EP 09 25 2052.7, completed Nov. 16, 2009; dated Nov. 24, 2009; (3 Page).
The extended European Search Report corresponding to European Application No. EP 09 25 2053.5, completed Nov. 24, 2009; dated Dec. 1, 2009; (3 Pages).
The extended European Search Report corresponding to European Application No. EP 09 25 2054.3, completed Jan. 7, 2010; dated Jan. 22, 2010; (3 Pages).

(56) References Cited

OTHER PUBLICATIONS

The extended European Search Report corresponding to European Application No. EP 09 25 2056.8, completed Jan. 8, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 8, 2011; dated Mar. 17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).
The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 4, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745.7, completed Mar. 19, 2013 and dated Apr. 11, 2013; (8 Pages).
The Extended European Search Report corresponding to EP 12 15 2989.5, completed Apr. 9, 2013 and dated Apr. 18, 2013; (9 Pages).
The Extended European Search Report corresponding to EP 08 73 2820.9, completed Jul. 2, 2013 and dated Jul. 9, 2013; (10 Pages).
The Extended European Search Report corresponding to EP 13 17 2008.8, completed Aug. 14, 2013 and dateded Aug. 28, 2013; (8 Pages).
The Extended European Search Report corresponding to EP 13 16 6382.5, completed Nov. 19, 2013 and dated Nov. 28, 2013; (8 Pages).
The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
The Extended European Search Report corresponding to EP 10 25 2112.7, completed Jul. 29, 2014 and dated Aug. 5, 2014; (8 pp).
The Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
European Search Report issued in corresponding European Application No. 19170951.8 dated Sep. 26, 2019, 7 pages.

* cited by examiner

SURGICAL CLIP APPLIER

CROSS-REFERENCE TO RELATED APPLICATION

This application claims the benefit of and priority to U.S. Provisional Patent Application No. 62/662,284 filed Apr. 25, 2018, the entire disclosure of which is incorporated by reference herein.

BACKGROUND

Technical Field

The present disclosure relates to surgical instruments. More particularly, the present disclosure relates to surgical clip appliers configured to apply surgical clips to tissue.

Description of Related Art

Surgical clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures.

Endoscopic surgical clip appliers having various sizes (e.g., diameters), that are configured to apply a variety of diverse surgical clips, are also known in the art, and are capable of applying a single or multiple surgical clips during an entry to the body cavity. Such surgical clips are typically fabricated from a biocompatible material and are usually compressed over tissue. Once applied to tissue, the compressed surgical clip terminates the flow of fluid therethrough.

SUMMARY

As detailed herein and shown in the drawing figures, as is traditional when referring to relative positioning on a surgical instrument, the term "proximal" refers to the end of the apparatus or component thereof which is closer to the user and the term "distal" refers to the end of the apparatus or component thereof which is further away from the user. Further, to the extent consistent, any or all of the aspects and features detailed herein may be used in conjunction with any or all of the other aspects and features detailed herein.

Provided in accordance with aspects of the present disclosure is a surgical clip applier including a handle assembly and an elongated assembly configured to releasably engage the handle assembly.

The handle assembly includes a housing, a trigger pivotably coupled to the housing, and a drive bar disposed within the housing and operably coupled to the trigger. The trigger is pivotable through a full actuation stroke from a first un-actuated position of the trigger to an actuated position of the trigger. The drive bar is translatable, in response to pivoting of the trigger, a full drive distance from a first un-actuated position of the drive bar to an actuated position of the drive bar. The drive bar includes a magnetic distal end portion.

The elongated assembly includes a proximal hub, an elongated shaft extending distally from the proximal hub, an end effector assembly supported at a distal end portion of the elongated shaft and including first and second jaw members, and an inner drive assembly extending through the proximal hub and the elongated shaft. The inner drive assembly is operably coupled to the end effector assembly such that translation of the inner drive assembly though the proximal hub and the elongated shaft moves the first and second jaw members from an open position to a closed position. The inner drive assembly includes a magnetic proximal end portion.

Upon engagement of the elongated assembly with the handle assembly, the magnetic proximal end portion of the inner drive assembly is configured to attract the magnetic distal end portion of the drive bar to move the drive bar to and retain the drive bar in a second un-actuated position of the drive bar wherein the drive bar is movable a reduced drive distance from the second un-actuated position of the drive bar to the actuated position of the drive bar. The movement and retention of the drive bar in the second un-actuated position pivots the trigger to and retains the trigger in a second un-actuated position of the trigger wherein the trigger is pivotable through a reduced actuation stroke from the second un-actuated position of the trigger to the actuated position of the trigger.

In an aspect of the present disclosure, with the elongated assembly engaged with the handle assembly, the trigger is movable through the reduced actuation stroke to thereby translate the drive bar through the reduced drive distance to, in turn, translate the inner drive assembly though the proximal hub and the elongated shaft to move the first and second jaw members from the open position to the closed position.

In another aspect of the present disclosure, the first and second jaw members are configured to retain a surgical clip therebetween such that, upon movement of the first and second jaw members from the open position to the closed position, the surgical clip is formed.

In still another aspect of the present disclosure, the handle assembly further includes a linkage assembly including at least one link coupling the trigger and the drive bar with one another such that pivoting of the trigger translates the drive bar.

In yet another aspect of the present disclosure, the inner drive assembly includes at least one actuation shaft.

In still yet another aspect of the present disclosure, the handle assembly further includes a latch mechanism configured to releasably engage the proximal hub of the elongated assembly with the housing of the handle assembly.

A surgical instrument provided in accordance with aspects of the present disclosure includes a handle assembly and an elongated assembly configured to releasably engage the handle assembly.

The handle assembly includes a housing, a trigger pivotably coupled to the housing, and a drive bar slidably disposed within the housing. The trigger is pivotable relative to the housing through a full actuation stroke from a first un-actuated position of the trigger to an actuated position of the trigger to translate the drive bar through the housing through a full drive distance from a first un-actuated position of the drive bar to an actuated position of the drive bar. The drive bar includes a magnetic distal end portion.

The elongated assembly includes a proximal hub, an elongated shaft extending distally from the proximal hub, an end effector assembly supported at a distal end portion of the elongated shaft, and an inner drive assembly operably coupled to the end effector assembly such that translation of the inner drive assembly actuates the end effector assembly. The inner drive assembly includes a magnetic proximal end portion, Upon engagement of the elongated assembly with the handle assembly, the magnetic proximal end portion of the inner drive assembly attracts the magnetic distal end portion of the drive bar to pull the drive bar to a second un-actuated position of the drive bar and pivot the trigger to a second un-actuated position of the trigger. As such, the trigger is thereafter pivotable relative to the housing through a reduced actuation stroke from the second un-actuated position of the trigger to the actuated position of the trigger to translate the drive bar through the housing through a reduced drive distance from the second un-actuated position of the drive bar to the actuated position of the drive bar.

In an aspect of the present disclosure, with the elongated assembly engaged with the handle assembly, the trigger is movable through the reduced actuation stroke to thereby translate the drive bar through the reduced drive distance to, in turn, translate the inner drive assembly though the proximal hub and the elongated shaft to actuate the end effector assembly.

In another aspect of the present disclosure, actuating the end effector assembly includes moving the first and second jaw members of the end effector assembly to a closed position to form a surgical clip disposed therebetween.

In still another aspect of the present disclosure, the handle assembly further includes a linkage assembly including at least one link coupling the trigger and the drive bar with one another such that pivoting of the trigger translates the drive bar.

In yet another aspect of the present disclosure, the inner drive assembly includes at least one actuation shaft.

In still yet another aspect of the present disclosure, the handle assembly further includes a latch mechanism configured to releasably engage the proximal hub of the elongated assembly with the housing of the handle assembly.

BRIEF DESCRIPTION OF THE DRAWINGS

Aspects and features of the present disclosure are described in detail with reference to the drawing figures wherein like reference numerals identify similar or identical structural elements and.

DETAILED DESCRIPTION

Figure 1:
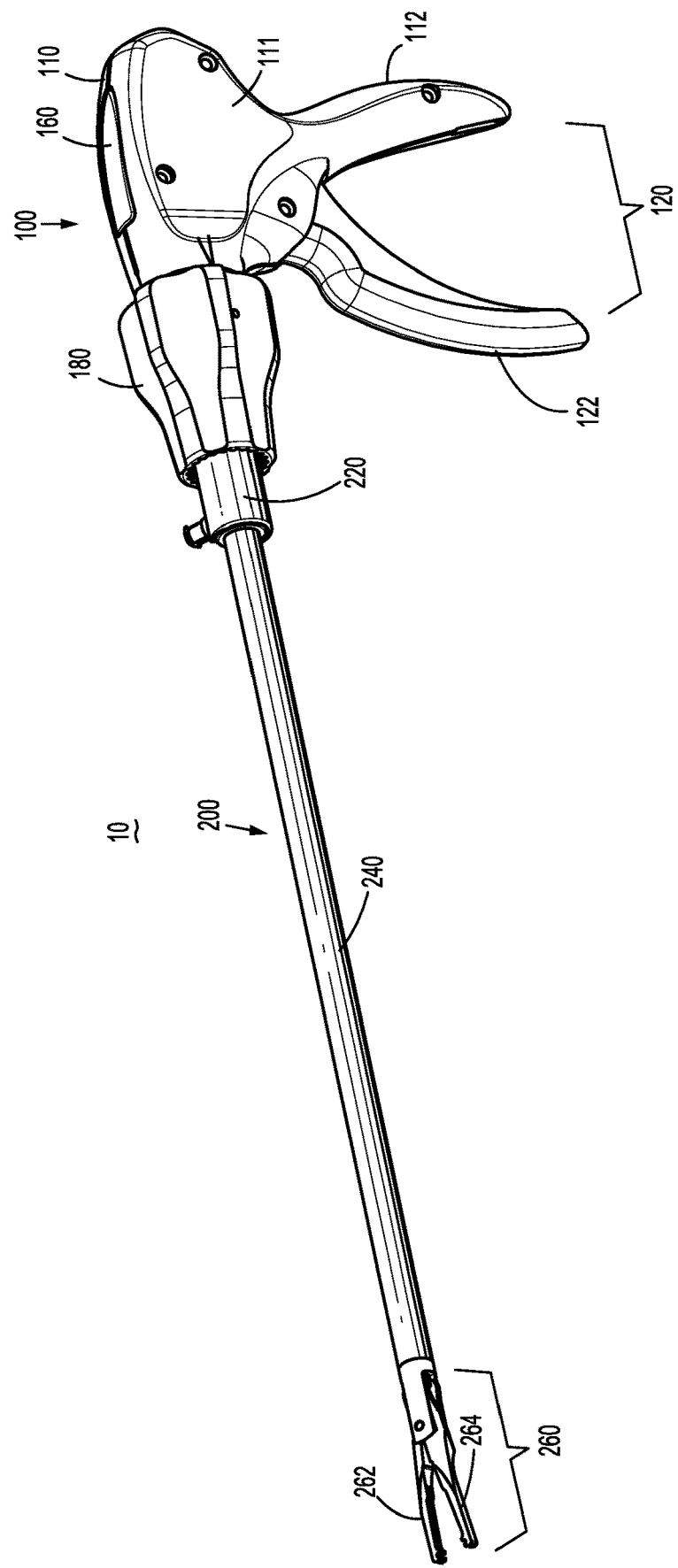
FIG. 1 is a perspective view of a surgical clip applier provided in accordance with the present disclosure including a handle assembly having an elongated assembly engaged therewith.
Figure 2:
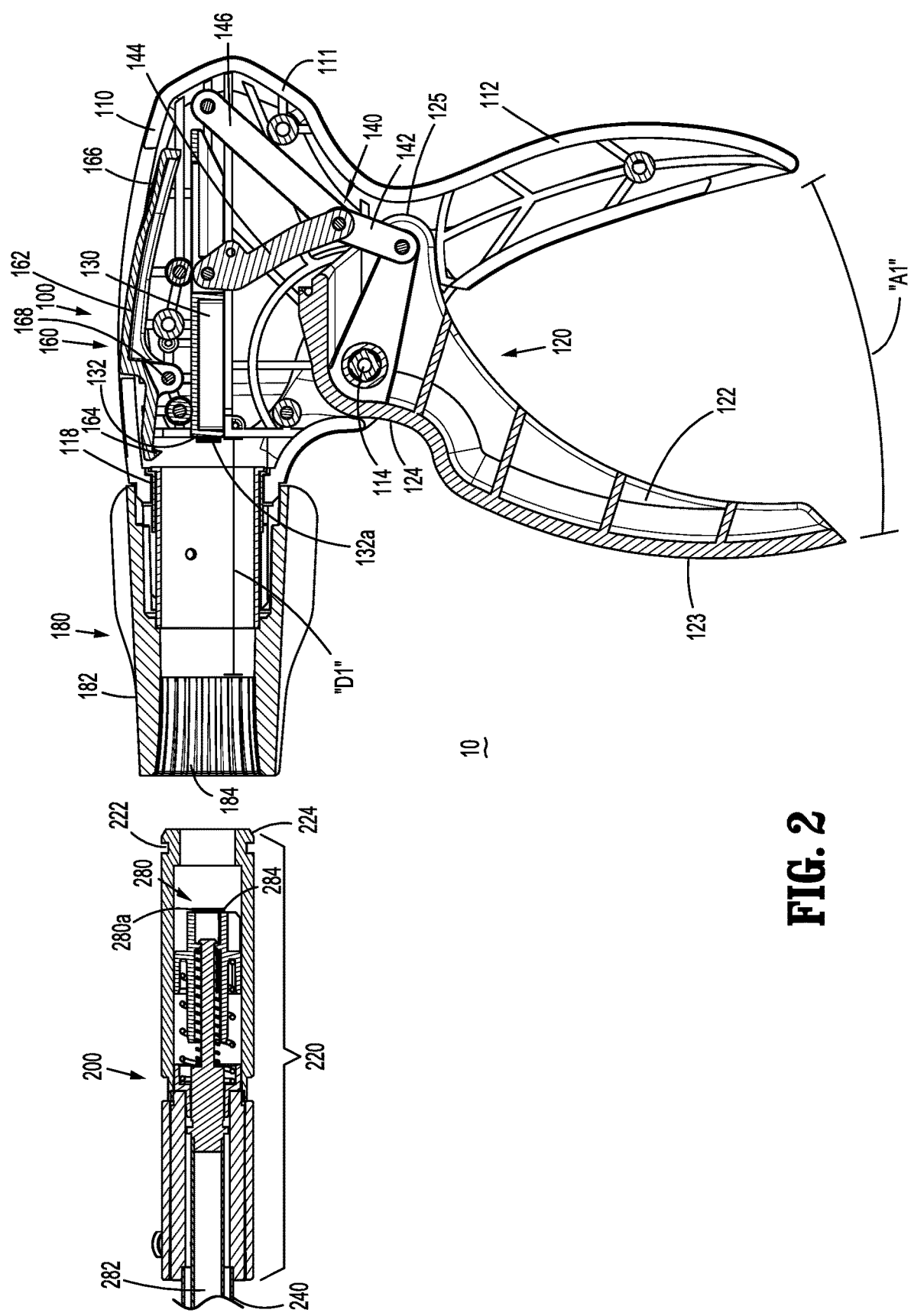
FIG. 2 is an enlarged, longitudinal, cross-sectional view of a proximal portion of the surgical clip applier of FIG. 1 with the elongated assembly disengaged engaged from the handle assembly.
Figure 3:
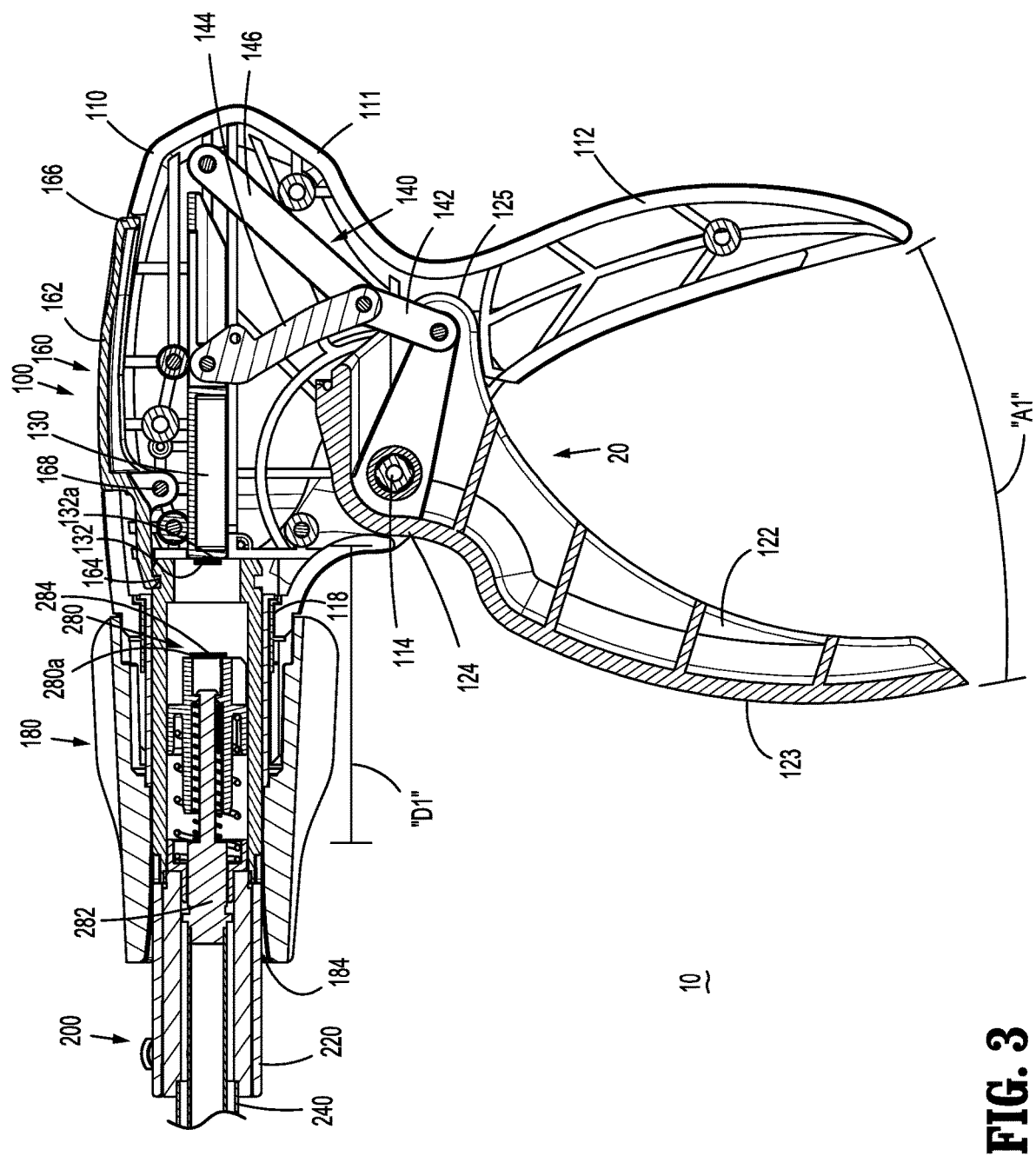
FIG. 3 is an enlarged, longitudinal, cross-sectional view of the proximal portion of the surgical clip applier of FIG. 2 with the elongated assembly moving into engagement with the handle assembly.
Figure 4:
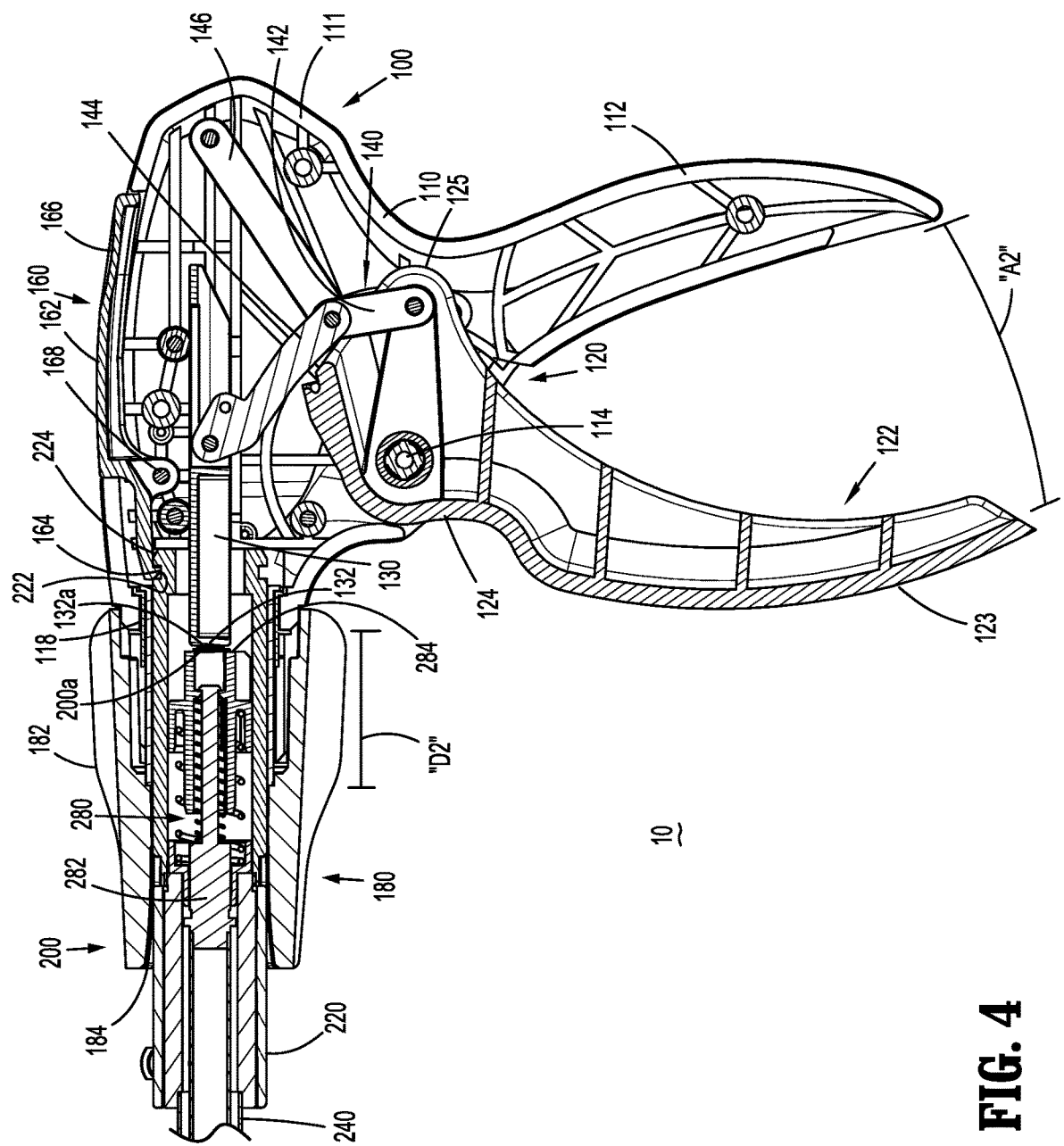
FIG. 4 is an enlarged, longitudinal, cross-sectional view of the proximal portion of the surgical clip applier of FIG. 2 with the elongated assembly fully engaged with the handle assembly.

Turning to FIGS. 1-4, a surgical clip applier embodying the aspects and features of the present disclosure is shown identified by reference numeral 10. Surgical clip applier 10 generally includes a handle assembly 100 and one or more elongated assemblies, e.g., elongated assembly 200, selectively connectable to handle assembly 100. Handle assembly 100 is configured to operate an elongated assembly upon connection thereto, and may be configured as a sterilizable, reusable component or otherwise configured such that handle assembly 100 may be used with different and/or additional elongated assemblies during the course of one or more surgical procedures. The one or more elongated assemblies may be configured as single-use disposable component, limited-use disposable component, or reusable component, depending upon a particular purpose. For the purposes herein, elongated assembly 200 is described, although it is understood that handle assembly 100 is configured for use with additional and/or alternative elongated assemblies.

Handle assembly 100 generally includes a housing 110, an actuation mechanism 120 operably associated with housing 110, a latch assembly 160 operably associated with housing 110, and a rotating receiver assembly 180 operably coupled to a distal portion of housing 110. Housing 110 of handle assembly 100 supports and/or encloses the operating components of handle assembly 100 and defines a body portion 111 and a fixed handle portion 112 depending from body portion 111. Body portion 111 of housing 110 includes an internal pivot post 114 extending transversely within body portion 111 and a distal opening 118 through which a proximal end portion of elongated assembly 200 extends when elongated assembly 200 is engaged with handle assembly 100.

Actuation mechanism 120 is operably supported by housing 110 and includes a trigger 122, a drive bar 130, and a linkage assembly 140. Trigger 122 includes a grasping portion 123, an intermediate pivot portion 124, and a proximal extension 125. Grasping portion 123 of trigger 122 extends downwardly from body portion 111 of housing 110 in opposed relation relative to fixed handle portion 112 of housing 110. Grasping portion 123 is configured to facilitate grasping and manipulation of trigger 122. Intermediate pivot portion 124 of trigger 122 is at least partially disposed within housing 110 and defines a pivot aperture 126 that is configured to receive pivot post 114 of housing 110 so as to enable pivoting of trigger 122 about pivot post 114 and relative to housing 110, e.g., between an un-actuated position, wherein grasping portion 123 of trigger 122 is spaced-apart relative to fixed handle portion 112, and an actuated position, wherein grasping portion 123 of trigger 122 is approximated relative to fixed handle portion 112.

Proximal extension 125 of trigger 122 is disposed on an opposite side of intermediate pivot portion 124 and, thus, pivot post 114, as compared to grasping portion 123 of trigger 122. As such, pivoting of grasping portion 123 to rotate in one direction, e.g., proximally towards fixed handle portion 112, pivots proximal extension 125 to rotate in the opposite direction, e.g., distally.

Linkage assembly 140 includes a first linkage 142, a second linkage 144, and a third linkage 146. First linkage 142 is pivotably coupled to proximal extension 125 of trigger 122 towards a first end portion of first linkage 142. Second and third linkages 144, 146, respectively, are each pivotably coupled to a second, opposite end portion of first linkage 142 at respective first end portions of second and third linkages 144, 146. A second, opposite end portion of second linkage 144 is pivotably coupled to drive bar 130, while a second, opposite end portion of third linkage 146 is pivotably coupled to body portion 111 of housing 110. Thus, the pivot point between first linkage 142 and proximal extension 125 of trigger 122, the pivot point between first linkage 142 and second and third linkages 144, 146, respectively, and the pivot point between second linkage 144 and drive bar 130 are movable pivot points (e.g., movable relative to housing 110), while the pivot point between third linkage 146 and housing 110 is a fixed pivot point (e.g., fixed relative to housing 110).

Upon actuation of trigger 122, e.g., proximal pivoting of grasping portion 123 of trigger 122 in a counterclockwise direction from the orientation illustrated in FIGS. 1-4, proximal extension 125 is moved in a distal, counterclockwise direction, thereby urging first linkage 142 towards drive bar 130. This movement of first linkage 142 towards drive bar 130, in turn, urges the first end portions of second and third linkages 144, 146, respectively, towards drive bar 130 to, in turn, urge the second end portion of second linkage 144 distally such that drive bar 130 is translated distally through body portion 111 of housing 110 from a proximal, un-actuated position thereof towards a distal, actuated position thereof. A biasing spring (not shown) may be provided to bias trigger 122 in a clockwise direction towards the un-actuated position thereof, thereby biasing drive bar 130 proximally towards its un-actuated position. Trigger 122 defines a maximum actuation stroke "A2" from its un-actuated position to its actuated position to, in turn, translate drive bar 130 a maximum drive distance "D1" from its un-actuated position to its actuated position.

Drive bar 130 is slidably disposed within body portion 111 of housing 110. At least a distal portion 132 of drive bar 130 includes a magnetic material 132a. A distal end portion 132 of drive bar 130 may be formed from a magnetic material, include a magnetic material coated thereon, may engage a magnet thereon or therein, or may otherwise be configured such that distal end portion 132 of drive bar 130 is magnetic.

Latch assembly 160 is configured to facilitate releasable locking engagement of elongated assembly 200 with handle assembly 100. Latch assembly 160, more specifically, includes a pivoting lever arm 162 operably disposed on and extending into body portion 111 of housing 110. Lever arm 162 includes an engagement finger 164 disposed towards one end thereof and a manipulatable portion 166 disposed towards the other end thereof with a pivot portion 168 disposed therebetween. Thus, upon depression of manipulatable portion 166 into housing 110 from a locked position to an unlocked position, engagement finger 164 is withdrawn upwardly and, upon release of manipulatable portion 166 and return thereof to the locked position, engagement finger 164 is returned downwardly. A torsion spring (not shown) disposed about pivot portion 168, or other suitable biasing spring in any suitable position, may be provided to bias lever arm 162 towards the locked position, although other configurations are also contemplated.

Rotating receiver assembly 180 is configured to receive a proximal end portion of elongated assembly 200 and to enable selective rotation thereof relative to housing 110. Rotating receiver assembly 180 includes a rotation knob 182 rotatably coupled to body portion 111 of housing 110 and extending distally therefrom. Rotation knob 182 defines a lumen 184 extending therethrough in communication with distal opening 118 of body portion 111 of housing 110 to enable insertion of a proximal portion of elongated assembly 200 therethrough and into operable engagement within housing 110.

Elongated assembly 200 generally includes a proximal hub 220, an elongated shaft 240 extending distally from proximal hub 220, an end effector assembly 260 disposed towards a distal end portion of elongated shaft 240, and an inner drive assembly 280 extending through proximal hub 220 and elongated shaft 240 and configured for operable coupling between handle assembly 100 and end effector assembly 260 when elongated assembly 200 is engaged with handle assembly 100 to enable firing of a surgical clip (not shown) about tissue.

Proximal hub 220 is configured for insertion through lumen 184 of rotation knob 182 and into body portion 111 of housing 110. Proximal hub 220 defines an annular recess 222 towards the proximal end thereof and a chamfered proximal edge 224. Thus, upon insertion of proximal hub 220 through lumen 184 of rotation knob 182 and into body portion 111 of housing 110, chamfered proximal edge 224 cams engagement finger 164 of latch assembly 160 over the outer surface of proximal hub 220 until engagement finger 164 is disposed in alignment with annular recess 222, wherein engagement finger 164 falls into engagement within annular recess 222 to engage proximal hub 220 and, thus, elongated assembly 200, with handle assembly 100. In order to disengage and remove elongated assembly 200 from handle assembly 100, manipulatable portion 166 of latch assembly 160 is depressed into housing 110 to withdraw engagement finger 164 from annular recess 222 and enable elongated assembly 200 to be pulled distally and removed from handle assembly 100. Proximal hub 220 and/or rotation knob 182 may further include complimentary keying features such that, upon insertion of proximal hub 220 into rotation knob 182, elongated assembly 200 is rotationally fixed relative to rotation knob 182 and such that rotation knob 182 and elongated assembly 200 are together rotatable relative to housing 110 upon rotation of rotation knob 182 relative to housing 110. Elongated shaft 240 extends distally from proximal hub 220 and supports end effector assembly 260 towards the distal end thereof.

End effector assembly 260 includes first and second jaw members 262, 264 pivotably engaged to one another to permit pivoting of jaw members 262, 264 relative to one another and elongated shaft 240 between an open position and a closed position. Jaw members 262, 264 are configured to receive and close, fire, or form a surgical clip about tissue, e.g., a surgical clip similar to those shown and described in U.S. Pat. No. 4,834,096, then entire contents of which are hereby incorporated herein by reference. However, it is contemplated that any suitable end effector assembly configured to close, fire, or form any suitable surgical clip(s) may be utilized with elongated assembly 200 in accordance with the present disclosure.

Inner drive assembly 280, as noted above, extends through proximal hub 220 and elongated shaft 240. Inner drive assembly 280 may include one or more actuation shafts 282 that cooperate to operably couple to jaw members 262, 264 of end effector assembly 260 towards a distal end portion (not shown) of inner drive assembly 280 such that translation, e.g., distal translation, of the one or more actuation shafts 282 of inner drive assembly 280 through elongated shaft 240 and relative to end effector assembly 260 pivots jaw members 262, 264 from the open position towards the closed position. A proximal end portion 284 of inner drive assembly 280, e.g., the proximal portion of one of the actuation shafts 282, is configured to couple to distal portion 132 of drive bar 130 upon engagement of elongated assembly 200 within handle assembly 100.

Proximal end portion 284 of inner drive assembly 280 includes a magnetic material 280a. Proximal end portion 284, more specifically, may be formed from a magnetic material, include a magnetic material coated thereon, may engage a magnet thereon or therein, or may otherwise be configured such that proximal end portion 284 of inner drive assembly 280 is magnetic.

Upon engagement of elongated assembly 200 within handle assembly 100, the magnetic distal end portion 132 of drive bar 130 and the magnetic proximal end portion 284 of inner drive assembly 280 attract and couple to one another in abutting, inter-fitting, or other suitable engagement to secure distal end portion 132 of drive bar 130 and proximal end portion 284 of inner drive assembly 280 relative to one another. As such, distal translation of drive bar 130 relative to housing 110, e.g., in response to actuation of trigger 122, urges inner drive assembly 280 distally through elongated shaft 240 and relative to end effector assembly 260 to pivot jaw members 262, 264 towards the closed position to close, fire, or form a surgical clip disposed between jaw members 262, 264. On the other hand, proximal translation of drive bar 130 relative to housing 110, in response to release or return of trigger 122, pulls inner drive assembly 280 proximally through elongated shaft 240 and relative to end effector assembly 260 to pivot jaw members 262, 264 back towards the open position.

Referring generally to FIGS. 1-4, as noted above, handle assembly 100 is configured such that trigger 122 defines maximum actuation stroke "A1" that, in turn, translates drive bar 130 maximum drive distance "D1." Inner drive assembly 280, as also noted above, is configured to translate through elongated shaft 240 and relative to end effector assembly 260 to pivot jaw members 262, 264 from the open position towards the closed position to close, fire, or form a surgical clip disposed between jaw members 262, 264. However, depending upon the configuration of the elongated assembly 200 utilized and/or the surgical clip (not shown) to be closed, fired, or formed, drive bar 130 may not need to translate the maximum drive distance "D1" in order to fully actuate the inner drive assembly 280 to fully close, fire, or form the surgical clip. In such instances where drive bar 130 is not required to translate the maximum drive distance "D1" in order to fully actuate inner drive assembly 280, a dead space may be created at the beginning and/or end of the maximum actuation stroke "A1" of trigger 122 (and, thus, the maximum drive distance "D1" of drive bar 130) wherein trigger 122 is being actuated to translate drive bar 130 but there is no effect on end effector assembly 260. This dead space effect may be undesirable by the user.

The present disclosure eliminates the aforementioned dead space effect utilizing the magnetic coupling of distal end portion 132 of drive bar 130 and proximal end portion 284 of inner drive assembly 280 with one another, although other suitable couplings eliminating this dead space effect are also contemplated. More specifically, distal end portion 132 of drive bar 130 and proximal end portion 284 of inner drive assembly 280 are configured such that, upon engagement of elongated assembly 200 within handle assembly 100, the magnetic attraction between distal end portion 132 of drive bar 130 and proximal end portion 284 of inner drive assembly 280 pulls drive bar 130 distally towards inner drive assembly 280 such that the magnetic distal end portion 132 of drive bar 130 and the magnetic proximal end portion 284 of inner drive assembly 280 attract and couple to one another, thus retaining drive bar 130 in a more-distal position as compared to the un-actuated position thereof. The distal pulling and retention of drive bar 130 in the more-distal position, in turn, pivots trigger 122 in a counterclockwise direction from the un-actuated position towards the actuated position and retains trigger 122 in the more-counterclockwise position. As such, the initial starting positions of trigger 122 and drive bar 130 are shifted (while the fully actuated positions thereof remain the same) such that, in use, trigger 122 is only capable of being actuated through a reduced actuation stroke "A2" to, in turn, translate drive bar 130 a reduced drive distance "D2." More specifically, the actuation stroke of trigger 122 and drive distance of drive bar 130 are reduced according to the actuation stroke and actuation distance required to pivot jaw members 262, 264 from the open position towards the closed position to close, fire, or form a surgical clip disposed between jaw members 262, 264, thereby eliminating any dead space. Thus, upon actuation, trigger 122 and drive bar 130 may be actuated through the reduced actuation stroke "A2" and reduced drive distance "D2," respectively, to the fully actuated positions thereof to pivot jaw members 262, 264 from the open position towards the closed position to close, fire, or form a surgical clip disposed between jaw members 262, 264 without the dead space effect.

As an alternative to the magnetic attraction between distal portion 132 of drive bar 130 and proximal end portion 284 of inner drive assembly 280 pulling drive bar 130 distally to engage inner drive assembly 280, or where the initial spacing between distal end portion 132 of drive bar 130 and proximal end portion 284 of inner drive assembly 280 is too great to enable magnetic attraction, trigger 122 may be primed by partially actuating trigger 122 until distal end portion 132 of drive bar 130 and proximal end portion 284 of inner drive assembly 280 engage one another and are held in engagement via the magnetic attraction therebetween, thereby retaining drive bar 130 and trigger 122 in their respective modified initial positions.

While use of a pair of magnetic materials 132a, 280a is shown and described in embodiments hereof, it is contemplated and within the scope of the present disclosure that a single magnetic material 123a or 280a may be used in combination with a complimentary ferromagnetic or magnetically attractive material (e.g., iron, nickel, cobalt, gadolinium, dysprosium and alloys such as steel that also contain specific quantities of ferromagnetic metals such as iron or nickel therein). It is further contemplated that an electromagnet may be incorporated into handle assembly 100 and/or elongated assembly 200, as understood by one skilled in the art, to achieve the intended purpose of magnetic materials 132a, 280a described herein.

As can be appreciated, depending upon the particular requirements of the elongated assembly utilized with handle assembly 100, the actuation stroke of trigger 122 and drive distance of drive bar 130 may not be reduced at all, may be reduced a relatively small amount, or may be reduced a relatively larger amount. Thus, handle assembly 100 provides a reliable feel without the dead space effect regardless of the particular configuration of the elongated assembly utilized therewith.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical clip applier, comprising:
   a handle assembly, including:
      a housing;
      a trigger pivotably coupled to the housing and pivotable relative thereto through a full actuation stroke from a first un-actuated position of the trigger to an actuated position of the trigger; and
      a drive bar operably coupled to the trigger such that pivoting of the trigger through the full actuation stroke translates the drive bar through the housing a full drive distance from a first un-actuated position of the drive bar to an actuated position of the drive bar, the drive bar including a magnetic distal end portion; and
   an elongated assembly configured to releasably engage the handle assembly, the elongated assembly including:
      a proximal hub;
      an elongated shaft extending distally from the proximal hub;
      an end effector assembly supported at a distal end portion of the elongated shaft, the end effector assembly including first and second jaw members; and
      an inner drive assembly extending through the proximal hub and the elongated shaft, the inner drive assembly operably coupled to the end effector assembly such that translation of the inner drive assembly though the proximal hub and the elongated shaft moves the first and second jaw members from an open position to a closed position, the inner drive assembly including a magnetic proximal end portion,
   wherein, upon engagement of the elongated assembly with the handle assembly, the magnetic proximal end portion of the inner drive assembly is configured to attract the magnetic distal end portion of the drive bar to move the drive bar to and retain the drive bar in a second un-actuated position of the drive bar wherein the drive bar is movable a reduced drive distance from the second un-actuated position of the drive bar to the actuated position of the drive bar, thereby pivoting the trigger and retaining the trigger in a second un-actuated position of the trigger wherein the trigger is pivotable through a reduced actuation stroke from the second un-actuated position of the trigger to the actuated position of the trigger.

2. The surgical clip applier according to claim 1, wherein with the elongated assembly engaged with the handle assembly, the trigger is movable through the reduced actuation stroke to thereby translate the drive bar through the reduced drive distance to, in turn, translate the inner drive assembly though the proximal hub and the elongated shaft to move the first and second jaw members from the open position to the closed position.

3. The surgical clip applier according to claim 2, wherein the first and second jaw members are configured to retain a surgical clip therebetween such that, upon movement of the first and second jaw members from the open position to the closed position, the surgical clip is formed.

4. The surgical clip applier according to claim 1, wherein the handle assembly further includes a linkage assembly including at least one link coupling the trigger and the drive bar with one another such that pivoting of the trigger translates the drive bar.

5. The surgical clip applier according to claim 1, wherein the inner drive assembly includes at least one actuation shaft.

6. The surgical clip applier according to claim 1, wherein the handle assembly further includes a latch mechanism configured to releasably engage the proximal hub of the elongated assembly with the housing of the handle assembly.

7. A surgical instrument, comprising:
   a handle assembly including a housing, a trigger pivotably coupled to the housing, and a drive bar slidably disposed within the housing, the trigger pivotable relative to the housing through a full actuation stroke from a first un-actuated position of the trigger to an actuated position of the trigger to translate the drive bar through the housing through a full drive distance from a first un-actuated position of the drive bar to an actuated position of the drive bar, the drive bar including a magnetic distal end portion;
   an elongated assembly configured to releasably engage the handle assembly, the elongated assembly including a proximal hub, an elongated shaft extending distally from the proximal hub, an end effector assembly supported at a distal end portion of the elongated shaft, and an inner drive assembly operably coupled to the end effector assembly such that translation of the inner drive assembly actuates the end effector assembly, the inner drive assembly including a magnetic proximal end portion,
   wherein, upon engagement of the elongated assembly with the handle assembly, the magnetic proximal end portion of the inner drive assembly attracts the magnetic distal end portion of the drive bar to pull the drive bar to a second un-actuated position of the drive bar and pivot the trigger to a second un-actuated position of the trigger such that the trigger is pivotable relative to the housing through a reduced actuation stroke from the second un-actuated position of the trigger to the actuated position of the trigger to translate the drive bar through the housing through a reduced drive distance from the second un-actuated position of the drive bar to the actuated position of the drive bar.

8. The surgical instrument according to claim 7, wherein with the elongated assembly engaged with the handle assembly, the trigger is movable through the reduced actuation stroke to thereby translate the drive bar through the reduced drive distance to, in turn, translate the inner drive assembly though the proximal hub and the elongated shaft to actuate the end effector assembly.

9. The surgical instrument according to claim 8, wherein the end effector assembly includes first and second jaw members configured to retain a surgical clip therebetween such that, upon actuation of the end effector assembly, the first and second jaw members are closed position to form the surgical clip.

10. The surgical instrument according to claim 8, wherein the handle assembly further includes a linkage assembly including at least one link coupling the trigger and the drive bar with one another such that pivoting of the trigger translates the drive bar.

11. The surgical instrument according to claim 8, wherein the inner drive assembly includes at least one actuation shaft.

12. The surgical instrument according to claim 1, wherein the handle assembly further includes a latch mechanism configured to releasably engage the proximal hub of the elongated assembly with the housing of the handle assembly.

* * * * *